(12) United States Patent
Zuckerbraun

(10) Patent No.: US 7,820,884 B2
(45) Date of Patent: Oct. 26, 2010

(54) DUAL PURPOSE WATERMELON: REDUCED SUGAR WATERMELON FOR TYPE 2 DIABETICS, AND POLLENIZER FOR SEEDLESS WATERMELONS

(75) Inventor: Eliezer Zuckerbraun, Ashdod (IL)

(73) Assignee: Gold Seed Co. LLC, Miami, FL (US)

( * ) Notice: Subject to any disclaimer, the term of this patent is extended or adjusted under 35 U.S.C. 154(b) by 194 days.

(21) Appl. No.: 12/120,806

(22) Filed: May 15, 2008

(65) Prior Publication Data

US 2009/0288183 A1 Nov. 19, 2009

(51) Int. Cl.
*A01H 1/00* (2006.01)
*A01H 5/00* (2006.01)
*A01H 5/10* (2006.01)

(52) U.S. Cl. ........................ 800/308; 800/260
(58) Field of Classification Search ................ 800/308
See application file for complete search history.

(56) References Cited

U.S. PATENT DOCUMENTS 6,759,576 B2 * 7/2004 Zhang et al. ................ 800/308

OTHER PUBLICATIONS

Weidong et al (2002, Cucurbit Genet. Coop. Rep. 25:30-31).*
Elmstrom et al (1981, J. Amer. Soc. Hort. Sci. 106:330-333).*

* cited by examiner

*Primary Examiner*—Anne Kubelik

(57) ABSTRACT

The invention relates to a diploid watermelon having fruit with approximately ⅓ lower sugar content than common watermelons found in the market place, and plant characteristics favorable for use as a pollenizer for commercial production of seedless watermelons. In addition to reduced sugar, fruit characteristics of the invention include a tough rind, firm flesh, distinct rind color, and small fruit. The watermelon plant of the invention has the characteristics of extended flowering duration, thin leaves, and long sprawling vines. The invention combining the above mentioned fruit and plant characteristics can serve the dual purpose of producing reduced sugar watermelon fruit, and pollinating seedless watermelons. This will in effect produce reduced sugar watermelons which are beneficial for consumers with type 2 diabetes as a byproduct of commercial seedless watermelon production making the product more economically feasible.

7 Claims, No Drawings

DUAL PURPOSE WATERMELON: REDUCED SUGAR WATERMELON FOR TYPE 2 DIABETICS, AND POLLENIZER FOR SEEDLESS WATERMELONS

RELATED PATENTS AND APPLICATIONS

U.S. Patent Documents

| | | |
|---|---|---|
| 6,355,865 | March 2002 | Elmstrom |
| 2003/0121075 | June 2003 | Barham, Warren S. |
| 2003/0163852 | August 2003 | Barham, Robert; et al. |
| 6,759,576 | July 2004 | Zhang, et al. |
| 2006/0137044 | June 2006 | Lanini; Brenda; et al. |

OTHER REFERENCES

American Diabetes Association website—accessed Mar. 17, 2008 Bassett, Mark J. (editor), 1986, Breeding Vegetable Crops, AVI Publishing Company, Inc.
Central Intelligence Agency website—accessed Mar. 17, 2008
Florida Cooperative Extension Service, Institute of Food and Agricultural Sciences, University of Florida, HS1079, January 2007
Glich et al., (Eds), 1993, Methods in Plant Molecular Biology & Biotechnology, CRC Press
Harvard School of Public Health website—accessed Mar. 17, 2008
Maynard, D. N. (editor), 2001, Watermelon Characteristics, Production and Marketing, ASHS Press
National Agricultural Statistics Service of USDA—January 2006
Rhodes & Dane, 1999, Gene List for Watermelon, Cucurbit Genetics Cooperative Report 22:71-77
University of Sydney—Glycemic Index and GI database—accessed Mar. 17, 2008
Zhang, Xing-ping & Jiang, Yi, 1990, Edible Seed Watermelons (*Citrullus lanatus* (Thunb. Matsum. Nakai) in Northwest China, Northwestern Agricultural University, China.

FIELD OF THE INVENTION

This invention is in the field of watermelon breeding, specifically relating to diploid watermelon plants producing fruit with reduced sugar content, and also serving the function of pollinating triploid watermelon plants for the commercial production of seedless watermelon fruit.

BACKGROUND OF THE INVENTION

Watermelon is an important horticultural crop with over 137,000 acres grown in the United States in 2005. The leading watermelon producing states are Florida, Georgia, Texas, and California with a combined total of 86,300 acres. (National Agricultural Statistics Service of USDA—January 2006)

The popularity of seedless (triploid) watermelon has increased over the last decade. During peak watermelon production in the U.S. market in 2005 and 2006, seeded watermelons only comprised 22% of the market and averaged four to five cents less per pound (Florida Cooperative Extension Service, Institute of Food and Agricultural Sciences, University of Florida, HS1079, January 2007).

Population of the United States is estimated at over 300 million as of July 2007 (Central Intelligence Agency website).

Of the 20.8 million Americans with diabetes, 90 to 95 percent have type 2 diabetes. (American Diabetes Association website). This amounts to 7% of the total population of the United States.

The glycemic index (GI) is a ranking of foods on a scale from 0 to 100 according to the extent to which they raise blood sugar levels after eating. Foods with a GI of 70 or above are considered high GI foods. Watermelon is rated at 72 which is considered a high GI. (University of Sydney Glycemic Index and GI database)

Glycemic index in watermelon can be lowered by decreasing its sugar content.

Lower GI foods have been shown to help control type 2 diabetes and improve weight loss. (Harvard School of Public Health—website)

The goal of plant breeding is to combine in a single variety or hybrid various desirable traits. Desirable traits may include resistance to diseases and insects, tolerance to heat and drought, reducing the time to crop maturity, greater yield, and better agronomic quality. Other desired traits may include particular nutrient content, color, fruit shape, as well as taste characteristics.

As with many different plants, watermelon contains a fruit part and a plant part. Each part contains different traits that are desired by consumers and/or growers, including such traits as flavor, texture, disease resistance, and appearance traits such as shape and color. Reduced sugar is a highly desirable trait for consumers with type 2 diabetes. The seedless trait in the watermelon fruit is also highly desired by consumers. Extended flowering in diploid watermelon plants is a trait sought after by growers of seedless watermelon.

Seeded watermelon plants are diploid and can be self-pollinated either by bees or by hand.

Seedless watermelon plants are triploid and must be pollinated by the pollen of diploid watermelon plants. The two primary methods currently in practice to pollinate seedless watermelon plants are; 1) planting traditional hybrid diploid varieties (e.g. Sangria produced by Syngenta, Inc.) in dedicated rows and harvesting and selling both the diploid fruit and the seedless fruit, or 2) inter planting between triploid watermelon plants within rows of triploid plants special pollenizer plants (e.g. SP-1 produced by Syngenta, Inc.), with plant characteristics especially favorable for pollination, which produce non-marketable fruit due their poor fruit quality, in particular a thin explosive rind making it difficult to harvest and transport the fruit. Due to the non-marketable fruit that these special pollenizer plants produce, they are generally referred to as "Non-Harvestable Pollenizers".

The present invention recognizes the need to provide consumers with type 2 diabetes a watermelon with reduced sugar and therefore with less total carbohydrates, and a lower glycemic index. The present invention also recognizes that a method of producing reduced sugar watermelons is needed that reduces the economic risk of producing this product which has a relatively limited market (less than 7% of the total market).

BRIEF SUMMARY OF THE INVENTION

The present invention uses a novel diploid watermelon to provide a product to the consumer segment, which includes those suffering from type 2 diabetes in an economical manner. According to the invention, there is provided a novel reduced sugar watermelon (hereinafter referred to as "dual purpose reduced sugar watermelon") and a method for producing it in an economical manner by using it as a pollenizer for seedless watermelon production. In other words, it will be produced as a byproduct of seedless watermelon production.

In addition to reduced sugar, the present invention includes a dual purpose reduced sugar watermelon with the following additional fruit traits enabling the successful production and marketing of this watermelon; 1) relatively firm flesh desired by consumers, 2) tough rind thereby reducing breakage of fruit during harvesting and transport, 3) rind color distinguishable from other watermelon fruit currently in the market in the United States, and 4) small fruit enabling consumers to purchase a "single portion". The small fruit also helps to increase flowering, which contributes to the invention's second purpose as a pollenizer for seedless watermelon production.

The present invention further includes a dual purpose reduced sugar watermelon comprising a plant with the following characteristics favorable for its second purpose as a pollenizer for seedless watermelon production; 1) extended flowering duration providing pollen to seedless watermelon plants over an extended time period, 2) thin leaves thereby shading seedless watermelon plants located in close proximity to a lesser degree, and 3) long thin sprawling vines providing pollen over a larger surface area.

Also included in this present invention is a method of producing reduced sugar watermelons as a byproduct making the reduced sugar watermelon crop more economically feasible. This is accomplished by using the reduced sugar watermelon plant as a pollenizer for seedless watermelon production. The reduced sugar watermelon plants can be planted within seedless watermelon fields as a pollenizer in any of the currently practiced manners, and the fruit of the reduced sugar watermelon can be harvested and sold.

The dual purpose reduced sugar watermelon of the invention is further enhanced by including resistance to various pests and herbicides via conventional plant breeding methods or genetic transformation.

The dual purpose reduced sugar watermelon of the invention is further enhanced by various flesh colors including orange or yellow or white or red via conventional plant breeding methods or genetic transformation.

DETAILED DESCRIPTION OF THE INVENTION

Development of Dual Purpose Reduced Sugar Watermelon

According to the present invention, a watermelon OW824 is selected having the characteristics of an extended flowering duration, small leaves with deep, non-overlapping leaf lobes, a long sprawling vine, firm flesh, tough rind, and low sugar content. In this example, the fruit of OW824 is relatively large, the rind and flesh are very firm, the seed size is very big, and the flesh is white. OW824 is a publicly available edible seed watermelon variety generally referred to as Xinjiang Edible Seed Watermelon.

Also according to the invention, a watermelon Mickylee (PI 601307) is selected for its rind color which is distinguishable from other watermelon fruit on the market in the United States. In this example, Mickylee has a firm red flesh, light green rind, and weighs 4 to 5 Kg. Mickylee is publically available from the USDA—AMS National Genetic Resources Program.

Also according to the invention, diploid inbred watermelon line GSX-26, a proprietary Gold Seed Co. breeding line is selected for its small size (average weight of 1.5 Kg.). In this example, GSX-26 has fruit with the following characteristics; jubilee type striped rind pattern, thin rind, sweet red flesh, oval shape with small seeds. The plant is of medium vigor, high fruit set, and with very early maturity.

The first step was to cross Mickylee to GSX-26, and then hybrid progeny were crossed to OW824 to form a three way cross.

This three way cross generated progeny having the characteristics of the dual purpose reduced sugar watermelon of the present invention as described in more detail below.

The initial cross of Mickylee X GSX-26 was made during the spring of 2005 in Israel. This hybrid was further crossed with OW824 in Summer 2005 in Israel. The three-way cross produced was self-pollinated in spring 2006 in Israel. The F2 generation was grown in the summer of 2006. Individuals with the set of traits required for the dual purpose reduced sugar watermelon were successfully identified and self-pollinated in the F2 population. A total of 4 selections were made. The 4 F3 lines were grown in Israel in Spring 2007 for further selection and evaluation. 1 F3 line was identified to best meet our breeding goals and advanced to the F4 generation. This one line, Escort-4, called 121-14, is fixed for every trait concerned. Escort-4 contains the traits that are illustrative of the traits of the dual purpose reduced sugar watermelon of the invention. Other examples of dual purpose reduced sugar watermelon lines with similar characteristics were 121-5 with yellow/pink flesh, 121-7 with white flesh, and 121-11 with slightly larger fruits and a different rind color.

Fruit: The fruit of the dual purpose reduced sugar watermelon, e.g. of Escort-4, has approximately ⅓ less sugar content compared to the most popular diploid varieties currently marketed. Fruit of Escort-4 and the most popular diploid variety currently on the market called Sangria (Syngenta, Inc.) were harvested at full maturity on May 7, 2008, and tested for Total Soluble Sugars (TSS) for comparison purposes as shown in Table 1 below. In this comparison, fruit of Escort-4 had an average TSS content of 32% less than Sangria.

TABLE 1

| Escort-4 | % TSS | Sangria | % TSS |
|---|---|---|---|
| Fruit #1 | 9.5 | Fruit #1 | 12.8 |
| Fruit #2 | 9.1 | Fruit #2 | 13.4 |
| Fruit #3 | 8.6 | Fruit #3 | 12.7 |
| Fruit #4 | 8.8 | Fruit #4 | 13.6 |
| Fruit #5 | 8.5 | Fruit #5 | 12.6 |
| Fruit #6 | 8.6 | Fruit #6 | 13.7 |
| Fruit #7 | 8.9 | Fruit #7 | 13 |
| Fruit #8 | 8.3 | Fruit #8 | 12.7 |
| Fruit #9 | 10.1 | Fruit #9 | 12.5 |
| Fruit #10 | 8.4 | Fruit #10 | 14 |
| Average | 8.9 | Average | 13.1 |

The flesh of the dual purpose reduced sugar watermelon, e.g. of Escort-4, is relatively firm. The flesh pressure when measured by a penetrometer (Model No. FT011 of Wagner Instruments, Greenwich, Conn. 06836) is in the range of approximately 2 lbs./inch to approximately 4 lbs./inch. The average flesh pressure is approximately 3 lbs./inch.

In addition, the fruit of the dual purpose reduced sugar watermelon, e.g. of Escort-4, compared to one of the more popular "non-harvestable" diploid pollenizers on the market called SP-1 (Syngenta, Inc.), has a much tougher rind, which resists breakage as opposed to the brittle fruit rind of SP-1 that splits easily and therefore can not be shipped easily if desired. Brittleness is conferred by a gene e (explosive rind, thin, and tender rind, bursting when cut (Rhodes & Dane, 1999, Gene List for Watermelon, Cucurbit Genetics Cooperative Report 22:71-77). The fruit of this invention does not contain this e gene and therefore has the ability to be harvested and transported long distances with minimal damage. For comparison purposes, fully mature fruit of Escort-4 and SP-1 were harvested on May 7, 2008 and measured for rind breakage pressure by a penetrometer (Model No. FT327 with a tip FT516—5/16 diameter of Wagner Instruments, Greenwich, Conn. 06836). The Escort-4 fruit broke at 16-22 lbs./in., whereas fruit of SP-1 broke at 7-10 lbs./in. The rind of Escort-4 resists more than double the pressure as compared to SP-1. See TABLE 2 below.

TABLE 2

| Escort-4 | Breakage Pressure (Lbs./Inch) | SP-1 | Breakage Pressure (Lbs./Inch) |
|---|---|---|---|
| Fruit #1 | 22.5 | Fruit #1 | 9.5 |
| Fruit #2 | 16 | Fruit #2 | 8.5 |
| Fruit #3 | 17 | Fruit #3 | 7.5 |
| Fruit #4 | 21 | Fruit #4 | 10 |
| Fruit #5 | 19.5 | Fruit #5 | 7 |
| Fruit #6 | 21 | Fruit #6 | 8 |
| Fruit #7 | 18.5 | Fruit #7 | 7.5 |
| Fruit #8 | 17.5 | Fruit #8 | 7.5 |
| Fruit #9 | 18 | Fruit #9 | 8.5 |
| Fruit #10 | 17 | Fruit #10 | 9.5 |
| Average | 18.8 | Average | 8.3 |

The fruit of the dual purpose reduced sugar watermelon of the invention, e.g. of Escort-4, can be distinguished from the fruit of all of the most popular commercially available seedless watermelon varieties marketed in the United States. The rind color of the dual purpose reduced sugar watermelon is preferably light green with slightly noticeable very thin medium green lines.

Preferably, the fruit size of the dual purpose reduced sugar watermelon, e.g. of Escort-4, is small being approximately in the range of about 5 to about 7 inches long, and in the range of about 4 to about 5 inches wide. Small fruit size was selected to decrease the load on the plant, thereby extending the duration of plant growth and flower production. Another advantage of the small fruit size is that it can be marketed as a single serving fruit providing an option for individuals wanting to enjoy watermelon without having the excess from a typically large fruit. The fruit of the dual purpose reduced sugar watermelon weighs approximately in the range of about 2 to about 7 lbs, preferably about 2 to about 6 lbs. The average weight for the fruits of the dual purpose reduced sugar watermelon is preferably about 4.0 lbs.

Flowering: The plants of the dual purpose reduced sugar watermelon, e.g. of Escort-4, are very vigorous and continue flowering over a relatively long period. The plant of this invention begins flowering approximately 7 days earlier than diploid reference variety Sangria. It continues to flower for approximately 7 weeks, which is when the most common seedless watermelon varieties finish harvesting. It therefore flowers during the entire flowering period of seedless watermelons currently in the market, thereby providing a continuous supply of diploid watermelon pollen to seedless watermelon plants during the critical time period.

Leaf: The leaves of the dual purpose reduced sugar watermelon, e.g. of Escort-4, are similar to the Xinjiang Edible Seed Watermelon. The leaves of the dual purpose reduced sugar watermelon preferably have a surface area approximately in the range of about 20 to about 70 $cm^2$, preferably about 22.5 to about 50 $cm^2$. The leaves of the dual purpose reduced sugar watermelon preferably have deep, non-overlapping leaf lobes. These thin leaves shade seedless watermelon plants located in close proximity to a lesser degree than diploid watermelon Sangria, which is a variety favored by many growers.

Vine: The vines of the dual purpose reduced sugar watermelon, e.g. of Escort-4, are long, thin, and sprawling similar to the Xinjiang Edible Seed Watermelon. Length of vine at first harvest is approximately 1.7 to 2.3 meters. Diameter of the vine is approximately 4 to 6 mm at the second node. The long sprawling vine provides pollen to seedless watermelon plants over an extended surface area.

Other Traits: The dual purpose reduced sugar watermelon, e.g. Escort-4, can be used either as donor of the set of traits disclosed above, or as the recurrent parent to develop additional dual purpose reduced sugar watermelon lines. In accordance with the invention, the dual purpose reduced sugar watermelon contains traits of disease resistance (e.g. *Fusarium wilt*, Anthracnose, Gummy Stem Blight, Powdery Mildew, and Bacterial Fruit Blotch), insect resistance (e.g. cucumber beetle, aphids, white flies and mites), salt tolerance, cold tolerance, and/or herbicide resistance added. In addition, the dual purpose reduced sugar watermelon contains various flesh colors (e.g. orange or white or yellow or red). These traits can be added to existing lines by using either the conventional backcrossing method, pedigree breeding method or genetic transformation. The methods of conventional watermelon breeding are taught in several reference books, e.g. Maynard, D. N. (editor), 2001, Watermelon Characteristics, Production and Marketing, ASHS Press; and Bassett, Mark J. (editor), 1986, Breeding Vegetable Crops, AVI Publishing Company, Inc. General methods of genetic transformation can be learned from published references, e.g. Glich et al., (Eds.), 1993, Methods in Plant Molecular Biology & Biotechnology, CRC Press.

Forms of the Dual Purpose Reduced Sugar Watermelon: Once the dual purpose reduced sugar watermelon lines are developed, several forms of dual purpose reduced sugar watermelon varieties can be used in commercial watermelon production. Specifically, these forms of dual purpose reduced sugar watermelon varieties include: (1) Open Pollinated Variety: The stable lines of the dual purpose reduced sugar watermelon are grown in isolated fields, at least 2,000 meters from other watermelon varieties. Pollination is conducted in the open fields by bees. Seeds are harvested from the seed production field when the fruit and seeds are fully developed. The seeds are dried and processed according to standard watermelon seed handling procedures. (2) Hybrid Variety: Two dual purpose reduced sugar watermelon lines, the male and female parents, are planted in the same field. Hand pollination is conducted. Only the seed from the female parent line is harvested and sold to the commercial grower for use.

Method of producing reduced sugar watermelons as a byproduct: In order to produce the reduced sugar watermelons in an economical manner the dual purpose reduced sugar watermelon can be used as a pollenizer for seedless watermelon production. It can be planted as a pollenizer in both of the most common currently practiced methods, which are; 1) planting the dual purpose reduced sugar watermelon in separate dedicated rows before and after every 2nd row of seedless watermelon plants, and the seedless watermelon fruit and the reduced sugar watermelon fruit would then be harvested and sold, or 2) inter planting between triploid watermelon plants with no dedicated space for the dual purpose reduced sugar watermelon plants within the same rows as the seedless watermelon plants between every 2nd or 3rd or 4th or 5th plant. Both the seedless watermelon fruit and the reduced sugar watermelon fruit would then be harvested and sold. Therefore, a dedicated field for production of reduced sugar watermelons is not necessary.

Deposit

Applicant has made a deposit of at least 2500 seeds of the Dual Purpose Reduced Sugar Watermelon line Escort-4 at The National Collections of Industrial and Marine Bacteria Limited (NCIMB), Ferguson Building, Craibstone Estate, Bucksburn, Aberdeen AB21 9YA, Scotland, UK under number NCIMB 41542 in order to illustrate the invention. This deposit of the Dual Purpose Reduced Sugar Watermelon line Escort-4 will be maintained in the NCIMB depository, which is a public depository, for a period of 30 years, or 5 years after the most recent request, or for the effective life of the patent, whichever is longer, and will be replaced if it becomes non-viable during that period. Additionally, applicant has satisfied all the requirements of 37 C.F.R. sections 1.801-1.809, including providing an indication of the viability of the sample. Applicant imposes no restrictions on the availability of the deposited material from the NCIMB; however, applicant has no authority to waive any restrictions imposed by law on the transfer of biological material or its transportation in commerce. Applicant does not waive any infringement of its rights granted under this patent.

The foregoing invention has been described in detail for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims. Thus, although the foregoing invention has been described in some detail in this document, it will be obvious that changes and modifications may be practiced within the scope of the invention, as limited only by the scope of the appended claims.

What is claimed is:

1. Seed of diploid watermelon line Escort-4, wherein representative seed of said line is deposited under NCIMB Accession No: 41542.

2. A diploid watermelon plant of line Escort-4, wherein representative seed of said line is deposited under NCIMB Accession No: 41542.

3. Pollen of the plant of claim 2.

4. An ovule of the plant of claim 2.

5. Fruit of the plant of claim 2.

6. A method for producing reduced sugar watermelons as a byproduct of seedless watermelon production, wherein the method comprises the steps of: a) planting a field with rows of triploid watermelon plants; b) planting dedicated rows of diploid watermelon plants according to claim 2 before and after every 2nd row of said triploid watermelon plants; c) allowing self-pollination of said diploid watermelon plants to obtain diploid watermelon fruit with reduced sugar content, and allowing pollination of said triploid watermelon plants by pollen of said diploid watermelon plants to obtain triploid seedless watermelon fruit; and d) harvesting said reduced sugar watermelon fruit and triploid seedless watermelon fruit.

7. A method for producing reduced sugar watermelons as a byproduct of seedless watermelon production, wherein the method comprises the steps of: a) planting a field with rows of triploid watermelon plants; b) inter planting diploid watermelon plants according to claim 2 before and after every 2nd or 3rd or 4th or 5th triploid watermelon plant within rows of triploid watermelon plants; c) allowing self-pollination of said diploid watermelon plants to obtain diploid watermelon fruit with reduced sugar content, and allowing pollination of said triploid watermelon plants by pollen of said diploid watermelon plants to obtain triploid seedless watermelon fruit; and d) harvesting said reduced sugar watermelon fruit and triploid seedless watermelon fruit.

* * * * *